Figure 1:
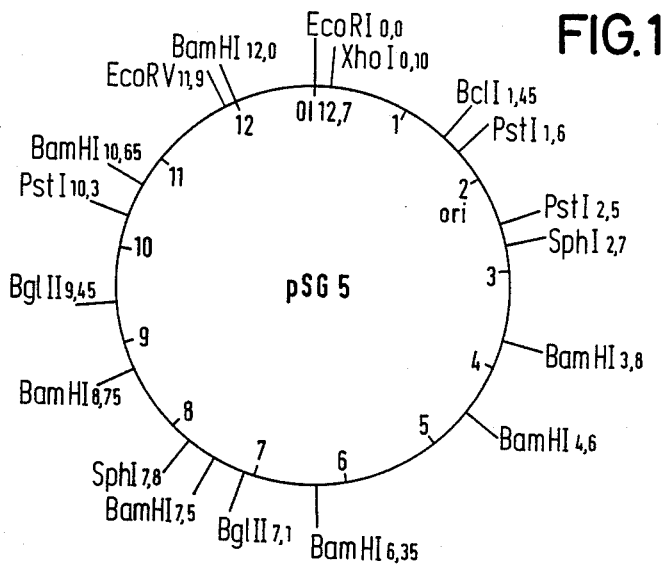

United States Patent [19]

Wohlleben et al.

[11] Patent Number: 4,880,746

[45] Date of Patent: Nov. 14, 1989

[54] STREPTOMYCETES PLASMID PSG5, A PROCESS FOR OBTAINING IT, AND ITS USE

[75] Inventors: Wolfgang Wohlleben; Agnes Schulte; Alfred Pühler, all of Bielefeld, Fed. Rep. of Germany

[73] Assignee: Hoechst Aktiengesellschaft, Frankfurt am Main, Fed. Rep. of Germany

[21] Appl. No.: 110,105

[22] Filed: Oct. 14, 1987

Related U.S. Application Data

[63] Continuation of Ser. No. 717,804, Mar. 29, 1985, abandoned.

[30] Foreign Application Priority Data

Mar. 31, 1984 [DE] Fed. Rep. of Germany ....... 3412093
Mar. 31, 1984 [DE] Fed. Rep. of Germany ....... 3412092

[51] Int. Cl.$^4$ .................. C12N 1/20; C12N 15/00; C12P 21/00; C12R 1/465
[52] U.S. Cl. .................................. 435/253.5; 435/68; 435/172.3; 435/252.33; 435/252.35; 435/320; 435/886; 536/27; 935/29; 935/72; 935/73; 935/75

[58] Field of Search .............. 435/68, 70, 71, 91, 435/172.1, 172.3, 252.3, 252.35, 243, 253, 320, 886, 253.5, 252.33; 536/27; 935/29, 72, 73, 75

[56] References Cited

U.S. PATENT DOCUMENTS 4,237,224 12/1980 Cohen et al. .......................... 435/68
4,416,994 11/1983 Nakatsukasa et al. .............. 435/253

OTHER PUBLICATIONS

Wohlleben et al., "Hybrid Plasmids with Streptomyces and Escherichia coli replicons", Chem. Abstr. 104: 46698c of Ger. Offen. DE 3,412,093.
Wohlleben et al., "Development of Shuttle Vectors Between Streptomyces Species and Escherichia coli", Chem. Abstr. 105: 1423p of Eur. Congr. Biotechnol., 3rd, 1984, 3:219–224.

Primary Examiner—James Martinell
Attorney, Agent, or Firm—Finnegan, Henderson, Farabow, Garrett and Dunner

[57] ABSTRACT

The plasmid pSG5 which, because of its molecular length of about 12.7 kb and its four unique restriction sites, can be used for the construction of plasmid vectors for Streptomycetes, for example of shuttle vectors between Streptomycetes and other microorganisms, can be isolated from a culture of *Streptomyces ghanaensis* DSM 2932.

3 Claims, 4 Drawing Sheets

STREPTOMYCETES PLASMID PSG5, A PROCESS FOR OBTAINING IT, AND ITS USE

CROSS REFERENCE TO A RELATED APPLICATION

This application is a continuation of application Ser. No. 717,804, filed Mar.29, 1985, now abandoned.

The invention relates to the new plasmid pSG5 which can be isolated from *Streptomyces ghanaensis* DSM 2932 (deposited in the Deutsche Sammlung von Mikroorganismen, Grisebachstrasse 8, D-3400 Gottingen, Federal Republic of Germany; Accession No. DSM 2932, and to the use of this plasmid for the preparation of plasmid vectors, for example shuttle vectors between Streptomycetes strains and other microorganisms.

The Streptomycetes plasmid pSG2, which was isolated from the *S. ghanaensis* strain ATCC 14672, is disclosed in European Patent Application with Publication No. 66,701. Since it is an endogenous plasmid, this plasmid is suitable for the construction of plasmid vectors which are to be inserted into *S. ghanaensis*.

It has now been found that a plasmid which is called pSG5 occurs in the *S. ghanaensis* strain DSM 2932. This plasmid is characterized by restriction sites (Table I) and by the restriction map (FIG. 1). 10 to 20 plasmids are contained in each cell. The plasmid has a molecular length of about 12.7 kilobase-pairs (kb), and thus is somewhat smaller than pSG2. Hybridization data show that there is no relationship between pSG2 and pSG5.

Apart from the size being somewhat smaller, pSG5 is distinguished from pSG2 by having at least four unique restriction sites for the restriction enzymes EcoRI, EcoRV, XhoI and BclI. Thus there are several possible ways of using this plasmid for genetic engineering purposes, for example for the construction of plasmid vectors.

It has also been found that pSG5 has an extended host range. For example, plasmid vectors prepared from pSG5 can be transformed into *S. lividans* and *S. geysirensis*.

Another advantage is that pSG5 is compatible with other Streptomycetes replicons, for example with the plasmids pSG2 from *S. ghanaensis*, pSVH 1 (European Patent Application with Publication No. 70,522) from *S. venezuelae* DSM 40755, SLP1.2 (U.S. Pat. No. 4,360,597, C. J. Thompson, J. M. Ward and D. A. Hopwood, Nature 286 (1980) 525; C.J. Thompson, T. Kieser, J. M. Ward and D. A. Hopwood, Gene 20 (1982) 51) from *S. lividans* and pIJ101 (T. Kieser, D.A. Hopwood, H.M. Wright and C. J. Thomson, Mol. Gen. Genet. 185 (1982) 223) from *S. lividans*. Thus, pSG5 can also be introduced into strains which already carry one of these plasmids.

This is of importance if the intention is to clone individual genes in different plasmids and to introduce them into one and the same cell. Moreover, the presence of compatible vector plasmids of different copy numbers allows the combination of individual genes in different numbers in one Streptomycetes strain. The existence of plasmid vectors of different compatibilities is of crucial importance both for the study of biosynthetic routes and for yield optimization.

It has been found, by transposon mutagenesis and cloning, that the replication region is located on the largest BamHI fragment (4.45 kb), namely in the region from 1 to 3 kb corresponding to FIG. 1. Thus, this "essential region" suffices for the construction of vectors which replicate in Streptomycetes.

The abovementioned 4.45 kb-long BamHI fragment, for example, is suitable for the construction of a "minimal replicon". When this fragment is circularized, then the plasmid obtained is distinguished by unique restriction sites for BclI, SphI, BamHI, EcoRI and XhoI. It has been shown for the latter four restriction sites that they are available for cloning. Moreover, on this fragment are also located restriction sites for PvuII (at 12.6, 3.2 and 3.6 kb as shown in FIG. 1), which are located outside the "essential region" and thus are available for cloning or further shortening. Furthermore, restriction sites for SstII (at 0.6, 1.8 and 3.65 kg as shown in FIG. 1) have been found, and the middle one of these is presumably located in the "essential region". In addition, at least five SalI restriction sites are present.

Figure 2:
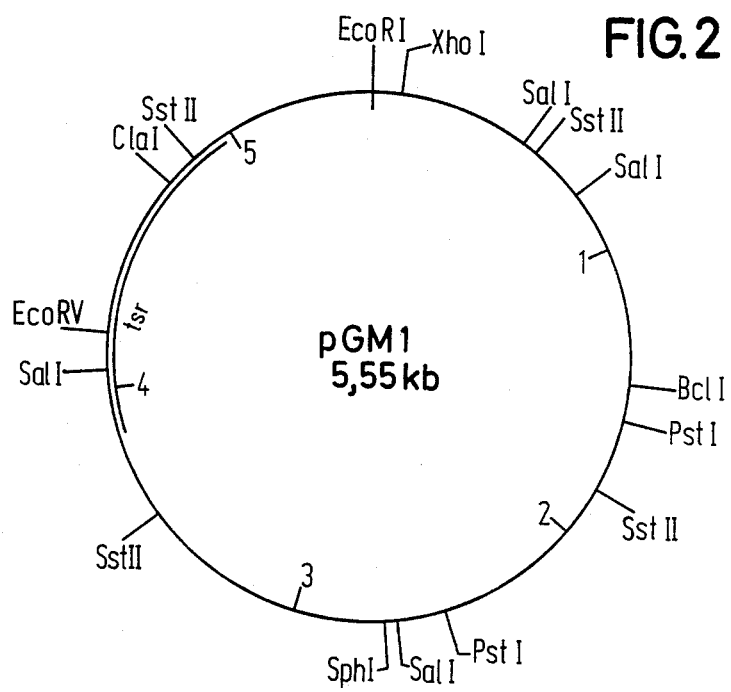

If the 4.45 kb BamHI fragment is ligated with the 1.1 kb BclI fragment from plasmid pIJ6 (Thompson et al., Nature, loc. cit.) having the thiostrepton resistance gene (tsr), then the hybrid plasmid pGM1, which replicates in Streptomycetes and can easily be selected on the basis of its thiostrepton resistance, is obtained. The unique restriction sites for EcoRI and XhoI, in particular, are available for the incorporation of foreign genes. FIG. 2 shows the restriction map of pGM1, in which only three SalI restriction sites are mapped in the replicon.

Figure 3:
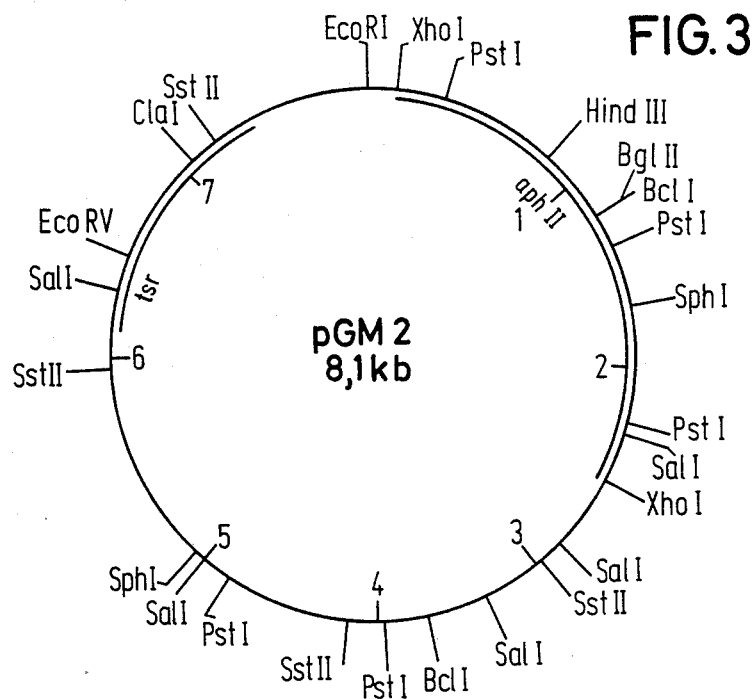
Figure 4:
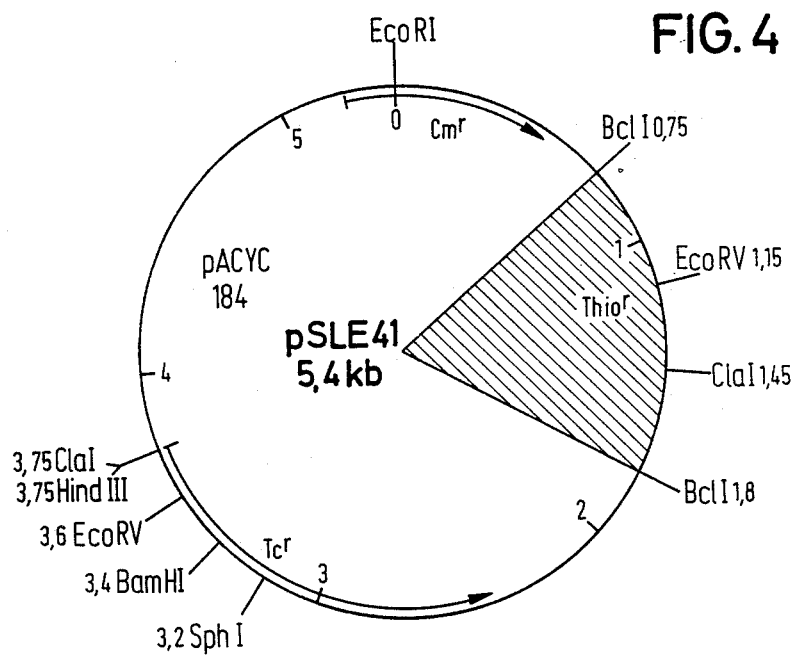

If, for example, the plasmid pGM1 is opened with XhoI and ligated with the 2.55 kb XhoI fragment from Tn5 (Jorgensen et al., Mol. gen. Genet. 177 (1977) 65; F.J. de Bruijn and J.R. Lupski, Gene 27 (1984) 131), which carries the neomycin resistance gene aphII which is effective in Streptomycetes and *E. coli*, then the hybrid plasmid pGM2 is obtained (FIG. 3, in which only three SalI restriction sites are mapped in the replicon). Thus, this plasmid has two markers which are effective in Streptomycetes and, given its molecular size of 8.1 kb and its unique restriction sites for EcoRI, HindIII, BglII, ClaI and EcoRV, is a good cloning vector. The BglII restriction site is in the aphII gene, while ClaI and EcoRV cut within the tsr gene. Thus, clonings using these enzymes can easily be verified by insertion inactivation.

The plasmid pSG5 and its shorter versions which contain the "essential region" are also suitable for the construction of so-called shuttle vectors. For example, if the plasmid pSG5 is fused with the *E. coli* plasmids pACYC184 or pBR325, then the hybrid plasmid can be multiplied not only in *E. coli* but also in Streptomyces species, in particular in *S. geysirensis* and *S. lividans*.

If the plasmid pACYC184 (Chang et al., J. Bacteriol. 134 (1978) 1141) is opened with BclI, and the linearized plasmid is ligated with the 1.1 kb BclI fragment from the plasmid pIJ6, the hybrid plasmid pSLE41 is obtained.

Figure 5:
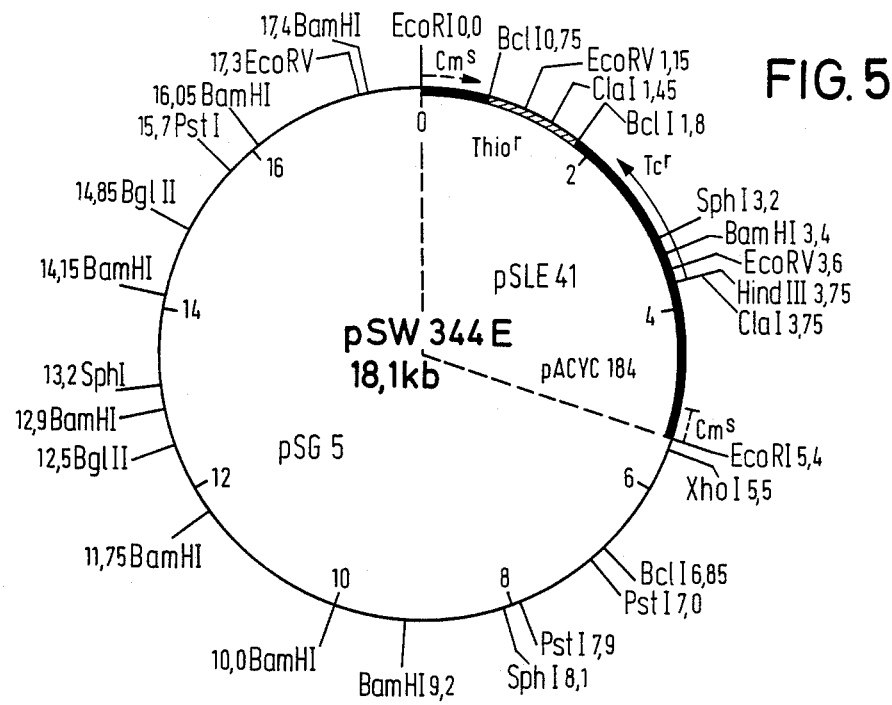

If, for example, the plasmids pSG5 and pSLE41 are fused via their EcoRI restriction sites, then the hybrid plasmid pSW344E (FIG. 5) is obtained, and this undergoes stable replication both in *E. coli*, because of the pACYC184 replicon and in Streptomycetes, because of the pSG5 replicon. Selection in *E. coli* is carried out by means of the tetracycline resistance of the pACYC184 component, while thiostrepton resistance can be used for selection in Streptomycetes. Thus, the plasmid pSW344E is an ideal shuttle vector between *E. coli* and Streptomycetes strains. The restriction sites for XhoI, HindIII and BglII are available, inter alia, for cloning of foreign DNA. The advantage of the shuttle vector is that a cloned Streptomycetes gene in E. coli can undergo genetic engineering modification and its function can be tested after transfer back into the Streptomycetes cell.

Figure 6:
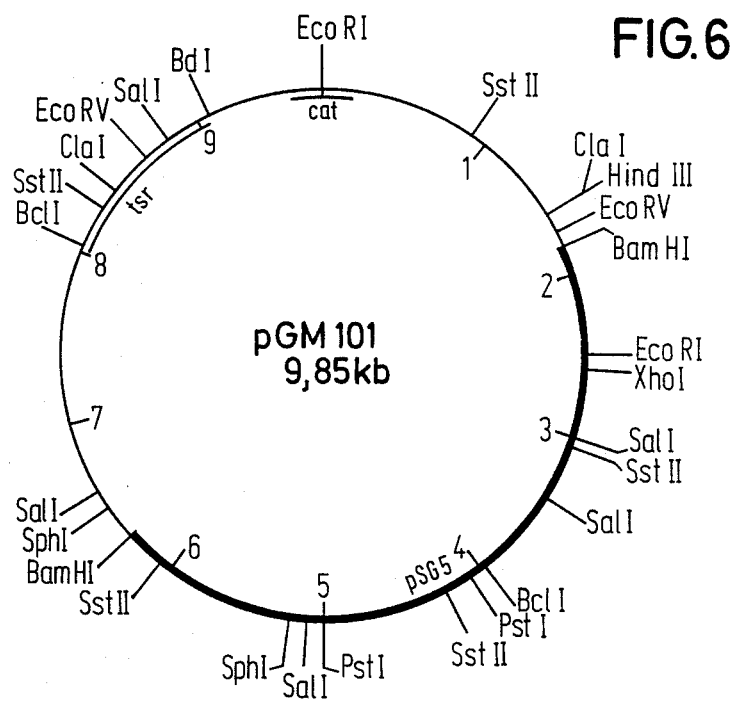

If pSLE41 is opened with BamHI and ligated with the 4.45 kg BamHI fragment from pSG5, then the result is the hybrid plasmid pGM101 (FIG. 6, in which only three SalI restriction sites are mapped in the replicon). This plasmid has unique restriction sites for HindIII and XhoI in non-essential regions. The selection markers available are chloramphenicol resistance (in E. coli) and thiostrepton resistance (in Streptomyces). The molecular size is 9.9 kb.

Figure 7:
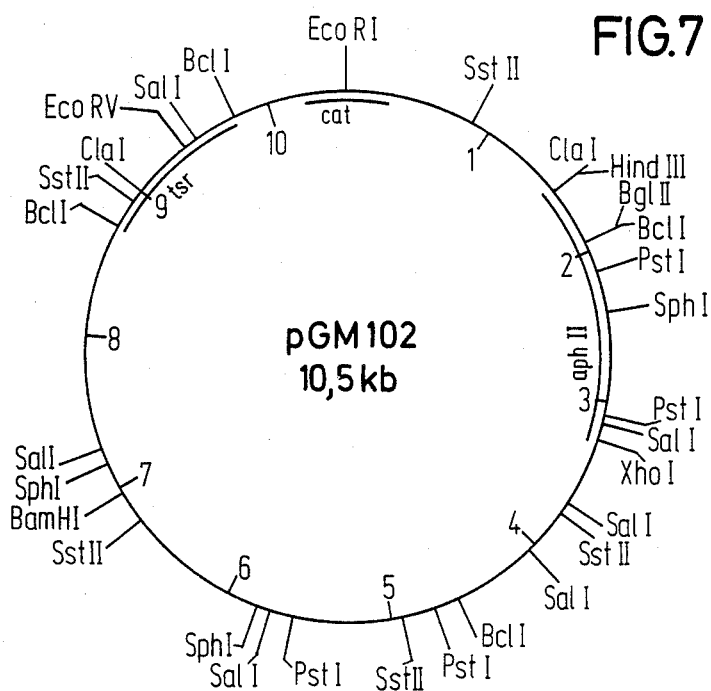

If the 1 kb HindIII-XhoI fragment is eliminated from pGM101, and in its place the 1.6 kb HindIII-XhoI fragment from Tn5, which carries the aphII resistance gene for neomycin, is inserted, then the hybrid plasmid pGM102 is produced (FIG. 7, in which only three SalI restriction sites are mapped in the replicon). The latter replicates in E. coli and S. lividans. Resistance to chloramphenicol and neomycin are available for selection in E. coli, and resistance to thiostrepton and neomycin are available for selection in S. lividans. It is possible to use for cloning in E. coli the unique restriction sites for EcoRI (inactivation of chloramphenicol resistance) and BglII (inactivation of neomycin resistance), and in Streptomycetes those for EcoRV (inactivation of thiostrepton resistance) as well as BglII, in addition the unique restriction sites for HindIII and XhoI.

German Patent Application No. P 34 12 093.9, with the title "Hybrid plasmids having a Streptomycetes replicon and an *Escherichia coli* replicon", which was filed on the same date, relates to shuttle vectors of this type. They are suitable for the production of antibiotics, enzymes or biologically active polypeptides, as is described for Streptomycetes plasmids in U.S. Pat. Nos. 4,273,875, 4,332,900, 4,338,400, 4,340,674, 4,343,906, 4,362,816, 4,362,817, 4,393,137, 4,401,761 and 4,416,994.

The isolation of the plasmid pSG5 from the strain S. *ghanaensis* DSM 2932 can be carried out in a manner known per se, as is described in, for example, European Patent Applications with Publication Nos. 66,701 and 70,522. The cultivation of the strain can be carried out in accordance with the former European Patent Application or with U.S. Pat. No. 3,674,866, Example 2.

The invention is illustrated in detail in the examples which follow. Unless otherwise specified, percentage data relate to weight in these examples.

EXAMPLE 1

Strain cultivation

The following media are suitable for cultivation for subsequent lysis:

| Lysis medium A | | Lysis Medium B | | Lysis Medium C | |
| --- | --- | --- | --- | --- | --- |
| glucose | 10 g | yeast extr. | 3 g | casein-peptone | |
| peptone | 4 g | peptone | 5 g | soymeal- | |
| yeast extr. | 4 g | malt extr. | 3 g | peptone broth | |
| KH₂PO₄ | 2 g | glucose | 10 g | (Merck 5459) | |
| K₂HPO₄ | 4 g | sucrose | 340 g | | 30 g |
| MgSO₄ | 0.5 g | glycine | 5 g | glycine | 10 g |
| glycine | 10 g | MgCl₂.6H₂O | 1 g | H₂O | 1 l |
| H₂O | 1 l | H₂O | 1 l | | |

About 100 ml of nutrient medium in a 500 ml conical flask are inoculated with a homogenized single colony and incubated at 30° C. in an orbital shaker (120 rpm) for 2-3 days.

EXAMPLE 2

Plasmid isolation

About 50 ml of a 3 day-old, homogenized liquid culture are harvested in JA-20 tubes in a Beckman J21C cooled centrifuge (10 min, 10,000 rpm, 25° C.) and washed once in TESu (10 mM tris HCl, 1 mM EDTA (pH 8), 10% sucrose). 2 g of cells are resuspended in 5 ml of lysozyme solution (0.3 M sucrose, 25 mM tris HCl (pH 8), 25 mM EDTA (pH 8), 4 mg/ml lysozyme) and incubated at 37° C. in an orbital shaker (100 rpm). After 30 - 45 min, the cells have been converted into protoplasts. The breakdown of the cell membrane and denaturation of the DNA is carried out by addition of 2.5 ml of lysis mix (0.3 M NaOH, 2% sodium dodecyl sulfate) and immediate vigorous mixing. Heat treatment for 10 minutes (70° C.) completes the lysis and denaturation. 800 µl of acid phenol/chloroform solution are added at room temperature (preparation of the acid phenol/chloroform solution: mix 500 ml of chloroform, 200 ml of H₂O, 500 g of phenol and 0.5 g of hydroxyquinoline and use the lower phase), in order to denature the proteins and renature the DNA. The mixture is thoroughly mixed in a shaker (®VORTEX) for about 20 sec, and then pelleted in a cooled centrifuge (15 min, 12,000 rpm, 4° C.).

7 ml of the plasmid-containing supernatant are then further purified in an ultracentrifuge: 7 g of CsCl, 7 ml of lysate and 0.2 ml of ethidium bromide solution (30 mg/ml) are mixed and centrifuged in an ultracentrifuge (®KONTRO TGA50) at 34000 rpm (20° C.) for 48 h. The plasmid band is visualized via its fluorescence on UV irradiation and is removed using a syringe. The solution is decolorized and dialyzed and is then ready for further investigations. It contains about 1 µg of plasmid DNA per 20 µl of solution.

EXAMPLE 3

Plasmid characterization

The pSG5 DNA is measured after imaging in an electron microscope. The specimen is prepared by known methods (J. Ferguson, R.W. Davis in "Advanced Techniques in Biological Electron Microscopy II", published by Springer, Berlin (1978) 123). Measurement of the length of the plasmid gives a figure of 4.2 µm.

In order to determine the number of restriction sites for various enzymes, pSG5 DNA is treated with various restriction endonucleases under appropriate incubation conditions for 1 h (see Table 2).

The total volume of the reaction mixture is 20 µl, of the following composition:

2 µl of incubation buffer concentrated 10-fold
x µl of DNA solution (containing about 0.5 µg of DNA)

1 μl of restriction enzyme (containing 1 unit)
17-x μl of H₂O

The reaction is stopped by addition of 5 μl of bromophenol blue solution. The fragments are separated by agarose gel electrophoresis (1% agarose in tris acetate buffer (0.04 M tris acetate, 0,0002 M EDTA)). The running time is 4 h and the voltage is 4 volt/cm length of gel. The length of the fragment can be calculated by comparison with a length standard (λ-DNA; cleaved with EcoRI and HindIII, lengths known (Phillipsen and Davis; Focus 1 (1979) 5)).

In addition to the number of restriction sites, the restriction analyses provide the fragment lengths and the total length of the plasmid. Finally, the restriction map can be drawn by suitable multiple digestions.

EXAMPLE 4

Construction of hybrid plasmids (a) Construction of pSLE41 pACYC184 DNA can be obtained from plasmid-bearing cells by known processes (Maniatis et al., Molecular Cloning, Cold Spring Harbor 1982). However, wild type *E. coli* cells possess a dam methylase and modify the DNA in such a manner that the necessary restriction with BclI is impossible. Thus, in this case, a dam⁻ mutant of *E. coli* is used to isolate the DNA.

The plasmid pIJ6 can be isolated from *Streptomyces lividans* TC14 by the techniques known for streptomycetes (see above).

For the cloning, the plasmid pACYC184 is linearized using the restriction enzyme BclI.

1 μg of DNA is incubated in cleavage buffer in the presence of 1 unit of BclI (manufactured by BRL, Neu-Isenburg) at 50° C. for 1 h. The reaction is stopped by phenol treatment, and the DNA is purified by ethanol precipitation. Subsequent treatment with alkaline phosphatase (from calf intestine, manufactured by Boehringer Mannheim) removes the 5'-phosphate ends of the DNA and prevents the religation of pACYC184. pIJ6 DNA is cut with BclI (for procedure, see above) in order to obtain the DNA fragment which carries the thiostrepton resistance.

The two DNA samples (in cleavage buffer) are mixed (0.1 μg of pACYC184 and 1 μg of pIJ6) and heated to 70° C. in order to open up H bridges. The reaction conditions are set by addition of mercaptoethanol (final concontration 10 mM) and ATP (0.1 mM). The DNA is incubated in the presence of 1 unit of T4 DNA ligase (Boehringer Mannheim) at 4° C. for 12 h.

*E. coli* is transformed with the DNA mixture (Maniatis et al.) and the cells are selected for resistance to tetracycline and chloramphenicol.

Individual colonies are subjected to rapid lysis to determine their size. A plasmid of size 5.4 kb (pACYC 184 4.3 kb +thio$^r$ 1.1 kb) is sought on an agarose gel. DNA is isolated (see above) from cells which carry a plasmid of the required length, and restriction analysis is used to elucidate whether the correct DNA fragment has been inserted. The restriction sites of the fragment are known (Kieser et al.), so that success of cloning can be verified.

(b) Preparation of the plasmid pSW344E.

The plasmid pSLE41 can be obtained from *E. coli* by known processes (Maniatis et al.). The plasmid pSG5 is isolated from *S. ghanaensis* 2932 as described above.

For the cloning, the two plasmids are linearized in parallel using EcoRI. 1 μg of DNA is incubated in cleavage buffer in the presence of 1 unit of EcoRI (manufactured by Boehringer Mannheim) at 37° C. for 1 h. The reaction is stopped by phenol treatment, and the DNA is purified by ethanol precipitation. pSLE41 DNA is advantageously also treated with alkaline phosphates in order to suppress religation. The DNA samples (in cleavage buffer) are then mixed (0.2 μg of pSLE41 and 1 μg of pSG5), heated to 70° C. and the ligase reaction conditions are set up by addition of mercaptoethanol (final concentration 10 mM) and ATP (0.1 mM). The mixture is incubated in the presence of 1 unit of T4 DNA ligase (Boehringer Mannheim) at 4° C. for 12 h. The mixture is then transformed into *E. coli* (Maniatis et al.), and colonies having tetracycline resistance and chloramphenicol sensitivity are selected.

Colonies having the appropriate pattern of resistance are subjected to rapid lysis to determine the plasmid sizes. DNA is isolated from cells which contain a plasmid of the required length (18.1 kb), and restriction analysis is used to elucidate whether the DNA provides the appropriate restriction pattern necessary if ligation of pSLE41 and pSG5 has taken place.

The hybrid plasmids pGM1, pGM2, pGM101 and pGM102 can be prepared in a similar manner.

EXAMPLE 5

Construction of a minimal replicon from pSG5

The plasmid pSG5 is isolated from *S. ghanaensis* DSM 2932 as described above. The plasmid pSLE41 can be obtained from *E. coli* by known processes (Maniatis et al.).

Fragments of pSG5 are cloned in pSLE41, namely the SphI, BamHI and BglII fragments in the SphI, BamHI and BamHI restriction sites of pSLE41. For the cloning, the two plasmids are linearized in parallel using the abovementioned enzymes (for manufacturers and incubation conditions, see Table 2). The reaction is stopped by phenol treatment, and the DNA is purified by ethanol precipitation (Maniatis et al.).

pSLE41 DNA is advantageously also treated with alkaline phosphatase in order to suppress religation (Maniatis et al.).

The DNA samples (in cleavage buffer) are then mixed (0.2 μg of pSLE41 and 1 μg of pSG5), heated to 70° C., and the ligase reaction conditions are set up by addition of mercaptoethanol (final concentration 10 mM) and ATP (0.1 mM). The mixture is incubated in the presence of 1 unit of T4 DNA ligase (Boehringer Mannheim) at 4° C. for 12 h. The mixture is then transformed into *E. coli* (Maniatis et al.) and colonies with chloramphenicol resistance and tetracyline sensitivity are selected. Colonies having the appropriate resistance pattern are subjected to rapid lysis to determine the plasmid sizes (T. Eckhardt, Plasmid 1 (1978) 584). DNA is isolated from cells which contain a plasmid of the required length, and restriction analysis is used to elucidate whether the expected fusion plasmids have been produced.

These plasmids are transformed into *S. lividans* TK 23 by customary processes (K.F. Chater, D.A. Hopwood, T. Kieser and C.J. Thompson: Gene Cloning in Streptomyces, Current Topics in Microbiol. and Immunol. 96, 69–95 (1982)) and selection for thiostrepton resistance is carried out. Plasmid DNa is isolated from thiostrep-tonresistant *S. lividans* colonies using standard procedures (T. Kieser, Factors Affecting the Isolation of cccDNA from *Streptomyces lividans* and *E. coli*, Plasmid 12, 19 (1984)) and its composition is checked.

All plasmids obtained from thiostrepton-resistant colonies carry the genes of the pSG5 plasmid which are necessary for replication. Thus, an appropriate "minimal replicon" can be identified from the overall results (in this case the 4.45 kb BamHI fragment), which can be further minimized by other cloning experiments and by comparative overlapping cloning.

TABLE 1

Number of restriction sites in the pSG5 plasmid for selected restriction enzymes

| Enzyme | Sites |
|---|---|
| KpnI | 0 |
| BglI | 0 |
| HpaI | 0 |
| HindIII | 0 |
| ClaI | 0 |
| EcoRV | 1 |
| EcoRI | 1 |
| XhoI | 1 |
| BclI | 1 |
| SphI | 2 |
| BglII | 2 |
| PstI | 3 |
| SalI | ≧5 |
| SstII | ≧5 |
| SmaI | ≧6 |
| BamHI | ≧7 |

TABLE 2

| | Restriction conditions | | |
|---|---|---|---|
| Enzyme | Incubation temperature in °C. | Manufactured by | Incubation buffer |
| BamHI | 37 | Boe | |
| BglI | 37 | Boe | |
| BglII | 37 | BRL | |
| BclI | 50 | Boe | |
| EcoRI | 37 | Boe | |
| EcRRV | 37 | Boe | in each case |
| ClaI | 37 | BRL | according |
| HindIII | 37 | Boe | to the |
| HpaI | 37 | Boe | manufacturer's |
| KpnI | 37 | BRL | recommendation |
| PstI | 37 | Boe | |
| SalI | 37 | BRL | |
| SmaI | 37 | Boe | |
| SphI | 37 | Boe | |
| SstI | 37 | BRL | |
| XhoI | 37 | BRL | |

Boe = Boehringer Mannheim, Mannheim
BRL = BRL, Neu-Isenb urg

We claim:

1. The plasmid pSG5 having a molecular length of about 12.7 kb, which is obtainable from a culture of *Streptomyces ghanaensis* DSM 2932.

2. A biologically pure culture of Streptomyces ghanaensis DSM 2932.

3. A hybrid plasmid comprising the plasmid pSG5 or its intact replication region.

* * * * *